US008389677B2

(12) United States Patent
Srinivas

(10) Patent No.: US 8,389,677 B2
(45) Date of Patent: Mar. 5, 2013

(54) ANTIOXIDANT POLYPEPTIDE AND A PROCESS FOR ISOLATION AND PURIFICATION OF THE SAME

(75) Inventor: Leela Srinivas, Mandya District (IN)

(73) Assignee: Adichunchanagiri Biotechnology and Cancer Research Institute, Karnataka (IN)

( * ) Notice: Subject to any disclaimer, the term of this patent is extended or adjusted under 35 U.S.C. 154(b) by 0 days.

(21) Appl. No.: 13/008,211

(22) Filed: Jan. 18, 2011

(65) Prior Publication Data

US 2011/0184146 A1 Jul. 28, 2011

(30) Foreign Application Priority Data

Jan. 22, 2010 (IN) .............................. 145/CHE/2010

(51) Int. Cl.
*C07K 2/00* (2006.01)
(52) U.S. Cl. ....................................................... 530/300
(58) Field of Classification Search .................. None
See application file for complete search history.

(56) References Cited

U.S. PATENT DOCUMENTS

2007/0014686 A1* 1/2007 Arnold et al. .................. 422/28

OTHER PUBLICATIONS

Smitha et al. Biochimi (2009) 91, 1156-1162.*
Potassium Permanganate, Merck Index (2006).*
Branen, "Toxicology and Biochemistry of Butylated Hydroxyanisole and Butylated Hydroxytoluene," J. Am. Oil Chem. Soc., vol. 52, pp. 59-63 (1975).
Handbook of Antioxidants, Second Edition, Revised and Expanded, Cadenas, et al. (ed.), Plenum, New York (2002).
Chaturvedi, et al., Ind. J. Dent. Res., 20(1):107-9 (2009).
Chethankumar, et al., "New Biological Activity Against Phospholipase $A_2$ by Turmerin, a Protein From *Curcuma longa* L.," Biol. Chem., vol. 389, pp. 299-303 (Mar. 2008).
Shalini, et al, "Fuel Smoke Condensate Induced DNA Damage in Human Lymphocytes and Protection by Turmeric (*Curcuma longa*)," Mol. Cell. Biochem. vol. 95, pp. 21-30 (1990).
Shalini, et al., "Lipid Peroxide induced DNA Damage; Protection by Turmeric (*Curcuma longa*)," Mol. Cell. Biochem. vol. 77, pp. 3-10 (1987).
Sies, "Physiological Society Symposium: Impaired Endothelial and Smooth Muscle Cell Function in Oxidative Stress," Exp. Physiol., vol. 82, pp. 291-295 (1997).
Srinivas, et al., "DNA Damage by Smoke: Protection by Turmeric and Other Inhibitors of ROS," Free Radical Biol. Med., vol. II, pp. 277-283 (1991).
Srinivas, et al., Turmerin: A Water Soluble Antioxidant Peptide From Turmeric (*Curcuma longa*), Arch. Biochem. Biophys., vol. 292, No. 2, pp. 617-623 (1992).
K. Chitra and K.S. Pillai, Guest Editorial, "Antioxidants in Health," Ind. J. Physiol Pharmacol, 46(1):1-5 (2002).
Ito, N., et al., "Carcinogenicity of Butylated Hydroxyanisole in F344 Rats," J. Natl. Cancer Inst. vol. 70, 343-352, 1983.
Srinvas et al., "Turmeric: The Indian Culinary Delight to the World" The Ind. J. Nutr. Dietet (2006) 43, 169-173.

\* cited by examiner

*Primary Examiner* — Nashaat Nashed
(74) *Attorney, Agent, or Firm* — Nixon & Vanderhye PC

(57) ABSTRACT

A polypeptide is isolated from Turmeric (*Curcuma longa* Linn) having molecular weight of about 8,000 Daltons. The polypeptide is highly water-soluble and absolutely non-toxic antioxidant, which is isolated using boiling water extraction. The polypeptide is an excellent antioxidant working at low concentration (of about 80 nM) to quench lipid peroxidation up to 90%. The polypeptide is highly effective against oxidative stress related diseases like arthritis, atherosclerosis, cardiovascular diseases, neurodegenerative diseases, cancer, cataract, malaria, bacterial and fungal infectious diseases.

1 Claim, 1 Drawing Sheet

Sephadex G-50 fractionation of Arishinin
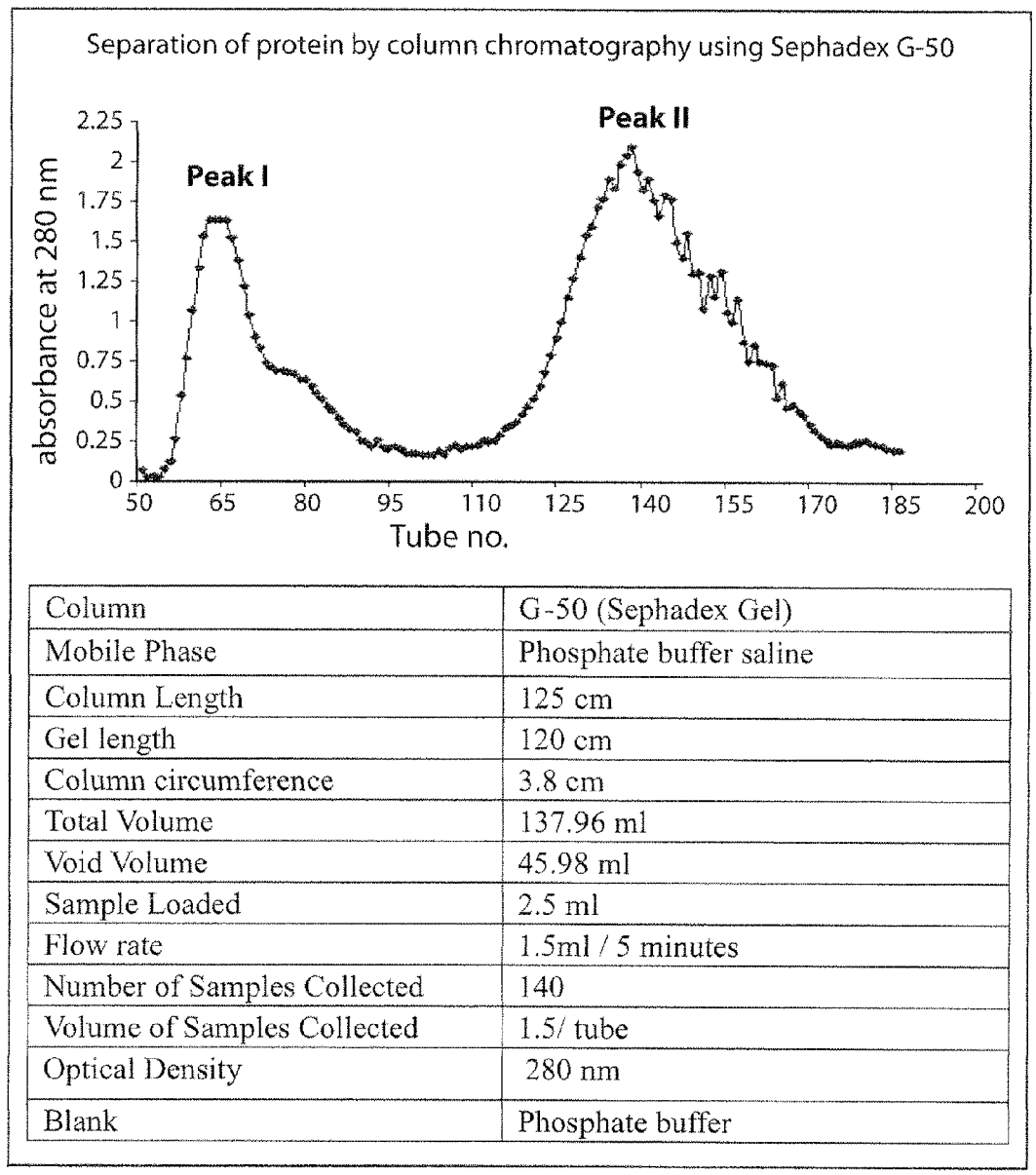
| Column | G-50 (Sephadex Gel) |
|---|---|
| Mobile Phase | Phosphate buffer saline |
| Column Length | 125 cm |
| Gel length | 120 cm |
| Column circumference | 3.8 cm |
| Total Volume | 137.96 ml |
| Void Volume | 45.98 ml |
| Sample Loaded | 2.5 ml |
| Flow rate | 1.5ml / 5 minutes |
| Number of Samples Collected | 140 |
| Volume of Samples Collected | 1.5/ tube |
| Optical Density | 280 nm |
| Blank | Phosphate buffer |

# ANTIOXIDANT POLYPEPTIDE AND A PROCESS FOR ISOLATION AND PURIFICATION OF THE SAME

CROSS-REFERENCE TO RELATED APPLICATION

This application claims priority rights under 35 U.S.C. §119 to Indian Provisional Patent Application number 145/CHE/2010 filed Jan. 22, 2010.

STATEMENT REGARDING FEDERALLY SPONSORED RESEARCH OR DEVELOPMENT

Not applicable

BACKGROUND

1. Technical Field

The present application relates to an antioxidant polypeptide and a process for isolation and purification of the same. The antioxidant polypeptide is water-soluble and is isolated from turmeric rhizome (*Curcuma longa* Linn). The polypeptide of the present invention is a potent non-toxic antioxidant and is useful in preventing many oxidative stress-related diseases like Arthritis, Atherosclerosis, Cardiovascular diseases, Cancer, Cataract and various Neurodegenerative diseases.

2. Related Art

Antioxidants are micronutrients that have gained an immense interest in recent years due to their ability to neutralize the action of free radicals (Cadenas, E., Packer, L., 1996, Hand Book of Antioxidants, Plenum, N.Y.). Oxygen-free radicals are reactive oxygen species (ROS) molecules which contain one or more unpaired electrons. These include Singlet oxygen, hydrogen peroxides, super oxide anions, peroxide, epoxide, hydroxyl radicals, etc. They are highly unstable molecules having very short half life. These free radicals are produced by oxidation reactions and by various metabolic processes in the body like life style practices, exposure to cigarette, beedi, even household fuel, forest fire and fuel emission smoke, nutritional deficiencies, exposure to gamma and U.V. irradiations, viral and bacterial infection, etc. Higher production of reactive oxygen reduces natural immunity of the body leading to oxidative stress. Oxidative stress acts as an etiological factor for cancer, cataract, arthritis atherosclerosis and cardiovascular disease. This can be prevented by augmenting the quantity of antioxidants by supplementation through external non-toxic dietary sources (Sies, 1997, Exp. Physiol., 82:291-295).

Effects of ROS on cellular metabolism are well documented. They can tilt the fine balance of oxidative stress, undermine defense against it and even result in cell death. However, oxidative stress induced by the oxidative burst of macrophages is an essential activity for killing microbes and ROS are also known to mediate many intracellular secondary and tertiary signaling cascades.

ROS attacks biological cellular targets like polyunsaturated fatty acids and ultimately the DNA of the cell. Thus, ROS can modify the very basic life-giving entity-DNA and thus is implicated in diseases like cancer.

To combat oxidative stress, antioxidants come in to play either to quench or scavenge radicals and render them ineffective. The source of antioxidants could be exogenous, mostly being derived from dietary sources (Chitra, K., and Pillai, K. S., 2002, India J. Physiol. Pharmacol., 46:1-5).

Chemical antioxidants such as Butylated Hydroxyl Anisole (BHA) and Butylated Hydroxy Toluene (BHT), although rated as good antioxidants, are reported to be carcinogenic and are reported to cause fore-stomach tumour in mice at more than 0.1% dose (Ito, N., et al., 1983, J. Natl. Cancer Inst., 70:343-347). BHA causes damages to liver and kidney, whereas BHT is much more toxic than BHA, since it is also a teratogen (Branien, A. L., 1975, J. Am. Oil Chem. Soc., 52, 59-63).

In light of the above, an antioxidant of plant origin, which is easily available, economically feasible, ethnically acceptable and culinary amenable and above all non-toxic in nature and easily dissoluble in body fluid, is required that can attenuate and prevent diseases—which is the need of the day.

There is enough evidence that Turmeric could provide at least one such above compound in prevention of diseases. Turmeric (*Curcuma longa* Linn) is widely used in India, Southeast Asia, Middle East, China and African countries as a major dietary spice compound, India being the largest grower and exporter of Turmeric. Ancient Indian medicine has propagated turmeric as a herb with the ability to provide glow and luster to the skin, a depilatory compound and also a spice with wound healing qualities (Leela Srinivas and Mukunda Chethan Kumar, 2006, Ind, J. Nutr. Dietet., 43:169; Chaturvedi, T. P., et al., 2009, Indian J. Dent. Res., 20(1):107-9).

In one of the earlier findings, the inventor of the present invention had also isolated a water-soluble antioxidant protein from Turmeric named as Turmerin. Although the Turmerin is essentially water-soluble, its higher molecular weight (of about 14 KDa) reduces its solubility and increases its dosage amount required for desired antioxidant activity. Thus, despite of being one of the best known plant antioxidants, Turmerin molecule had some inherent drawbacks.

Accordingly, the conventionally known antioxidant molecules, including Turmerin, are observed to suffer from one or more of the problem such as high toxicity, low solubility, high-dosage requirement, etc.

From the foregoing, it is evident that the discovery and development of new antioxidant molecule which could overcome some or all of the drawbacks associated with the molecules of the prior art.

BRIEF SUMMARY

A main object of the present invention is to provide an antioxidant molecule which overcomes some or all of the limitations associated with the prior art.

Accordingly, one of the objects of the present invention is to provide an antioxidant molecule which has low molecular weight and easily soluble in water (high solubility) and has high bioavailability.

Another object of the present invention is to provide an antioxidant molecule which is non-toxic to human beings, preferably a plant-derived antioxidant.

Another object of the present invention is to provide an antioxidant molecule which has high efficacy (antioxidant activity) at minimally low dosage.

Yet another object of the present invention is to provide an antioxidant molecule which is economically feasible and highly useful in preventing ROS induced diseases like arthritis, atherosclerosis, cardiovascular diseases, neurodegenerative diseases, cancer, cataract, malaria, bacterial and fungal infectious diseases.

Other objects and preferred embodiments and advantages of the present invention will become more apparent from the following description of the present invention when read in conjunction with the accompanying examples, figures and tables, which are not intended to limit the scope of the present invention.

The present exemplary embodiments are directed to a molecule (a polypeptide) that satisfies the needs as identified above. For example, an exemplary antioxidant polypeptide molecule has a molecular weight of about 8000 Daltons (8

KDa) and is highly soluble in water. The antioxidant polypeptide molecule of the exemplary embodiment is isolated from Turmeric (*Curcuma longa*) and is tested to be a completely non-toxic molecule. The exemplary antioxidant polypeptide has the property to prevent lipid peroxidation up to about 90% at a low dosage of about 80 nM.

The present exemplary embodiment also provides a process for purification of a polypeptide from Turmeric (*Curcuma longa*), the process comprising the steps of:
(i) sterilizing the rhizomes of Turmeric;
(ii) drying the sterilized rhizomes and crushing it into powdered form;
(iii) making a suspension of the turmeric powder in water (at a temperature of about 100° C.) and vortexing the suspension for about 1 to 4 hours;
(iv) centrifuging the above suspension in the range of about 8,000 rpm to about 10,000 rpm at a temperature in the range of about 1° C. to about 4° C. for a period of about 15 to about 25 minutes;
(v) filtering the supernatant obtained in step (iv), preferably using Whatman NO:1 filter paper, and lyophilizing the filtrate to obtain Aqueous Turmeric Extract;
(vi) filtering Aqueous Turmeric Extract using gel-filtration to pool-out molecules of the size of about 8 KDa; and
(vii) purifying the above isolate by dialyzing it against double distilled water extensively with nominal molecular weight cut-off membrane.

The present exemplary embodiment provides a purified polypeptide, isolated and purified from the Turmeric rhizome by the process as described above and wherein the said polypeptide having antioxidant properties.

Primarily, the present exemplary embodiment provides for an antioxidant polypeptide obtained from Turmeric (*Curcuma longa*), said polypeptide comprising an amino acid sequence at least 80% identical to SEQ ID NO:1 (as identified in the Detailed description of the invention) and having molecular weight of about 8 KDa.

These and other features, aspects and advantages of the present invention will become better understood with reference to the following description and appended claims.

BRIEF DESCRIPTION OF THE DRAWING

FIG. 1 provides a graphical depiction of the fractionation of Arishinin showing separation of protein by column chromatography using Sephadex G-50.

DETAILED DESCRIPTION OF EXEMPLARY EMBODIMENTS

The presently preferred exemplary embodiment provides for an antioxidant polypeptide molecule which has a molecular weight of 8000 Daltons (8 KDa) and is highly soluble in water, The antioxidant polypeptide molecule is isolated from Turmeric (*Curcuma longa*) and is found to be a non-toxic molecule. The polypeptide molecule purified from the Turmeric is termed as 'Arishinin' by the present inventor.

It is found by the present inventor that the Turmeric (*Curcuma longa*) have, in addition to the already known Turmerin protein, at least one other potent antioxidant polypeptide which has a lower molecular weight, high solubility and high bioavailability. This polypeptide is purified by the present inventor and is found to have molecular weight of about 8 KDa. It is also surprisingly found by the present inventor that this polypeptide (named Arishinin by the inventor) is highly soluble in water (solubility in water found to be in the range of from about 0.6 mg/ml to about 1.1 mg/ml), non-toxic to animals and possess high efficacy in very low dosages. It is observed by the present inventor that the polypeptide in accordance with the present invention, Arishinin, inhibits lipid peroxidation up to 90% at 80 nM concentration, thus showing a very good antioxidant activity at minimally low doses. The peptide was tested for toxicity in in vitro and in vivo tests and it was observed by the inventor that the polypeptide (Arishinin) is absolutely non-toxic to animals. Further purification was achieved by liquid chromatography using Sephadex G-50 and confirmed by HPLC and MS-MALDI.

The present polypeptide is also effective in quenching hydroxyl radical which mainly attacks DNA. It can prevent ROS induced diseases like Cancer, Heart disease, Cataract, snake bite, malaria, bacterial and fungal infection. Arishinin is non-toxic and hence does not have side effects. The health benefit resulting in the usage of antioxidant protein Arishinin extends to any health condition where reactive oxygen species is a factor to contend with, thus it is a disease preventive bio-molecule.

The present polypeptide (Arishinin) is a highly improved molecule, in comparison with the earlier known polypeptides including Turmerin and otherwise, in terms of its low molecular weight and high biological activity where relatively very low doses of Arishinin are sufficient to attain high anti-oxidative effect. More particularly, to achieve 80-90% prevention of lipid peroxidation, it requires about 180 nM of Turmerin whereas only 80 nM of the present polypeptide (Arishinin) is sufficient to achieve same order of activity. Further, the presently discovered polypeptide displace serine and metallo antiprotease activity, anti-inflammatory activity, anti-malarial, anti-microbial, anti-fungal activity which essentially differs from the earlier known polypeptide Turmerin. The HPLC and mass spectrum MALDI shows a substantially purified protein profile.

A partial amino acid sequence of the purified polypeptide revealed the following sequence:

SEQUENCE ID NO: 1
L-C-P-L-V-E-A-S-L-S-E-L-L-D-G-T-A-F-G-I-C-P-L-F-

N-N-K-S-I-T

The SEQ ID NO:1 is a partial sequence occurring in the native polypeptide. However, there could be few gaps due to non-ionization of certain amino acids.

The SEQ ID NO:1 was subjected to BLAST (Basic local alignment search tool; Altschul, S. F., et al., J. Mol. Biol., 215, 403-410, 1990) and EXPASY (Expert Protein Analysis System) analysis to determine the homology, if any with any existing polypeptide sequence or corresponding nucleotide sequence (or degenerate variants thereof) encoding the SEQ ID NO:1 or any variant thereof. The search results drew a blank, and indicate that the sequence is unique. There is no homologous sequence detected. However, it is found that the amino acids in the sequence identified as SEQ ID NO:1 are susceptible to limited modifications, additions, deletions or substitutions and, therefore, the homology of the sequence found to be present in the polypeptide is about 80% of the SEQ ID NO:1 at different times and in different conditions.

The phrase "amino acid" as used herein is broadly defined to include modified and unusual amino acids as defined in WIPO Standard ST. 25, and incorporated herein by reference.

The term "homology" as used herein means a value obtained by a BLAST (Basic local alignment search tool; Altschul, S. F., et al., J. Mol. Biol., 215:403-410, 1990). The homology in the amino acid sequence may be calculated by a BLAST search algorithm.

The process for isolation and purification of the present polypeptide (Arishinin) from the Turmeric is also provided in accordance with the present invention as: washing rhizomes of Turmeric with 0.1-0.5% of Potassium permanganate or 0.2-0.5% nitric oxide, but preferably 0.2% of $KMnO_4$ to make the rhizome devoid of microbes and germs. Potassium permanganate is preferred because it is less corrosive and is universally accepted as a decontaminant due to its capacity to eliminate the surface-adhering bacteria and fungi.

After sterilization of the rhizomes, drying the washed Rhizome either by shade drying or keeping at a temperature in the range of 35° to 42° C., preferably at 40° C. in an oven. Grind the dried rhizomes into fine powder such that it passes through British pharmacopeia 100 mesh sieve. Then suspend the resulting turmric powder in boiling double distilled water (100° C.) for 15 minutes, preferably for five minutes and vortexing for a period of about 1-4 hours, preferably one hour. Centrifugation of the suspension is carried out in the range of 8,000 rpm to 10,000 rpm, preferably at 8,000 rpm. During the centrifugation, the temperature is being maintained in the range of about 1° C.-4° C., preferably 4° C. The period of centrifugation is about 15-25 minutes, preferably about 20 minutes. After centrifugation, filter the supernatant using two layers of Whatman no-1 filter paper. The filtrate is then concentrated by lyophilization which contains the water-soluble antioxidant polypeptide Arishinin of 8 KDa. For further purification, the concentrate is subjected to Gel permeation chromatography using Sephadex G-50 column (Vt—240 ml, Vo—80 ml) to get partially purified Arishinin. To obtain fully purified Arishinin, dialyze the obtained Arishinin against double distilled water extensively with about 1-4 KDa preferably 2 KDa cut off dialysis membrane at 4-8° C. preferably at about 4° C. for about 48-72 hrs preferably for about 64 hours. This process depicts the general steps involved in the isolation and purification of the polypeptide. There are several variations possible of the above described method with various omissions and insertions without deviating from the spirit of the invention and in one of the embodiment, all such variations are included.

In order to identify the best mode of the invention and to standardize the steps, the present inventor has carried out the isolation and purification by employing several variations, which are described herein by means of Examples and preferred embodiments, none of which are intended to limit the scope of the invention.

Preparation of Aqueous Turmeric Extract 10 g of fine Turmeric powder as suspended on 300 ml of boiling double distilled water (100° C.) and vortexed for 4 hrs. The resultant suspension was centrifuged at 10,000 rpm for a period of 20 minutes at 4° C. Supernatant obtained was filtered through Whatman paper No. 1 filter paper and concentrated by lyophilisation. The resultant extract is the Aqueous Turmeric Extract (ATE). Total protein present in ATE was estimated by Bradford's method. Total protein yield is shown in Table 1 below:

TABLE 1

Total yield of Arishinin under various treatment conditions

| Sl. number of Examples | Treatment | Total soluble protein In Turmeric powder (mg/10 g of Turmeric) | Arishinin yield In Turmeric powder (mg/10 g of Turmeric) |
| --- | --- | --- | --- |
| Example 1 | 10 g of turmeric powder in 100 ml of boiling distilled water | 6 ± 0.5 | 0.2 ± 0.05 |
| Example 2 | 10 g of turmeric powder in 200 ml of boiling distilled water | 7 ± 0.5 | 0.25 ± 0.05 |
| Example 3 | 10 g of turmeric powder in 250 ml of boiling distilled water | 9 ± 0.5 | 0.32 ± 0.06 |
| Example 4 | 10 g of turmeric powder in 300 ml of boiling distilled water | 10 ± 0.5 | 0.39 ± 0.02 |

As per one of the most preferred embodiment, it can be observed from the Table 1 that the total yield was maximum by using 300 ml of boiling double distilled water. Hence, it was considered ideal for isolating the water-soluble antioxidant peptide Arishinin from Turmeric powder. Results are mean±S.D for three independent experiments.

Purification of Arishinin from Aqueous Turmeric Extract (ATE)

ATE containing 2 mg protein was loaded on to the Sephadex G-50 column ($V_T$=240 ml, $V_O$=80 ml) and eluted with 0.1M Tris HCl, pH –7.4 containing 0.1 M NaCl and flow rate was 1.7 ml/5 min, Fractions were monitored at 280 nm. Two peaks were obtained namely Peak I and Peak II. Peak II depicts the polypeptide of the present invention (Arishinin) as shown in FIG. 1 and the Gel filtration chromatography profile of Aqueous Turmeric Extract. Peak II was pooled, concentrated and dialyzed against double distilled water at 4° C. using 2 KDa cut off dialysis membrane for 74 hrs. SDS PAGE showed the approximate molecular weight of the protein is 8,000 Daltons. The antioxidant activity was done by TBARS and Hydroxy radical scavenging assay compared to standard antioxidant like BHA, Curcumin and α-tocopherol as positive controls. Cell viability test by Tryphan blue exclusion method was done to test the toxicity of Arishinin.

A exemplary separation of protein by column chromatography using Sephadex G-50 is depicted in FIG. 1.

The quantification of water-soluble antioxidant polypeptide Arishinin, isolated by the process described in Examples 1 to 4 (as depicted in Table 1 above) was determined by the following methods. Protein estimation was done by Bradford's method (Bradford, M. M., 1976, Analytical Biochem., 7:248-254) with an absorption maximum at 595 nm and results shown in Table 1. The antioxidant activity of Arishinin was evaluated by Thio Barbituric Acid Reactive Substance (TBARS) (Shimasaki, H., et al., 1984, Biochem. Biophys. Acta, 792:123-129) and Deoxyribose method/Hydroxyl radical scavenging assay (Halliwell, B., et al., 1981, Methods of Biochemical Sciences, 33:59-90) with absorption maximum at 535 nm by using BHA, alpha tocopherol and Curcumin as standard antioxidants. The antioxidant activity of Arishinin is shown in Table 2. Cell viability test by Tryphan blue exclusion method (Phillips, H. J., 1973; Kruse P. F., Patterson M. K., eds., pp. 406-408) was done to check the toxicity of Arishinin and experiment showed that Arishinin was not toxic.

TABLE 2

Antioxidant potential of Arishinin in both TBARS and Hydroxy Radical Scavenging Assay

| SL. NO | Antioxidants | CONCEN-TRATION | INHIBITION (%) TBARS | INHIBITION (%) Hydroxyl radical |
|---|---|---|---|---|
| 1 | α-tocopherol | 400 μM | 92 ± 1% | 88 ± 2% |
| 2 | Curcumin | 400 μM | 72 ± 1.5% | 68 ± 3% |
| 3 | BHA | 400 μM | 84 ± 1.5% | 80 ± 1% |
| 4 | Crude extract | 50 μg | 75 ± 2% | 72 ± 1.5% |
| 6 | Arishinin | 80 nM | 90 ± 1% | 90 ± 3% |

Results are mean ± S.D for three independent assays each performed in triplicate Arishinin at 80 nM dose gives 90% inhibition of reactive oxygen species. Since Arishinin is required at a very low dose of 80 nM, it is very cost-effective and is absolutely non-toxic.

The inference which can be drawn from the Table 2 is that the Arishinin of the present application is a potent antioxidant than other known standard antioxidants. A pertinent point is that, Arishinin is required at a very small dose to achieve almost the same antioxidant activity exhibited by α-tocopherol, BHA and Curcumin. These antioxidants are required at 400 μM concentration as compared to 80 nM of Arishinin. Another important point is these standard antioxidants could prove toxic at higher doses as exemplified by BHA and BHT.

Although the present invention has been described in considerable detail with reference to certain preferred embodiments thereof, other embodiments and equivalents are possible. Even though numerous characteristics and advantages of the present invention have been set forth in the foregoing description, together with functional and procedural details, the disclosure is illustrative only, and changes may be made in detail, especially in terms of the procedural steps within the principles of the invention to the full extent indicated by the broad general meaning of the terms in which the appended claims are expressed. Thus various modifications are possible of the presently disclosed process without deviating from the intended scope and spirit of the present invention. More particularly, the process for purification/isolation of the same, as depicted in the present invention, is seemingly a simplified and generalized one and there are several trivial variations possible. Accordingly, in one embodiment, such modifications of the presently disclosed process and polypeptide are included in the scope of the present invention. In addition to the process, there are functional variants of the polypeptide, which are similar in nature, size, structure and function to that of the polypeptide identified in the present invention, all of which are included in the scope of the present invention.

Any element in a claim that does not explicitly state "means for" performing a specified function, or "step for" performing a specific function, is not to be interpreted as a "means" or "step" clause as specified in 35 U.S.C. §112, ¶6.

What is claimed is:

1. A purified antioxidant polypeptide of SEQ ID NO: 1 obtained from Turmeric (*Curcuma longa*), and having molecular weight of about 8 kDa as determined by gel-permeation.

* * * * *

SEQUENCE LISTING

```
<160> NUMBER OF SEQ ID NOS: 1

<210> SEQ ID NO 1
<211> LENGTH: 30
<212> TYPE: PRT
<213> ORGANISM: Curcuma longa Linn

<400> SEQUENCE: 1

Leu Cys Pro Leu Val Glu Ala Ser Leu Ser Glu Leu Leu Asp Gly Thr
1               5                   10                  15

Ala Phe Gly Ile Cys Pro Leu Phe Asn Asn Lys Ser Ile Thr
            20                  25                  30
```